United States Patent
Reinhardt

(10) Patent No.: US 12,427,050 B2
(45) Date of Patent: Sep. 30, 2025

(54) ANTI-SNORING DEVICE

(71) Applicant: Thomas J. Reinhardt, Kassel (DE)

(72) Inventor: Thomas J. Reinhardt, Kassel (DE)

( * ) Notice: Subject to any disclaimer, the term of this patent is extended or adjusted under 35 U.S.C. 154(b) by 716 days.

(21) Appl. No.: 17/910,234

(22) PCT Filed: Nov. 17, 2020

(86) PCT No.: PCT/DE2020/100975
§ 371 (c)(1),
(2) Date: Sep. 8, 2022

(87) PCT Pub. No.: WO2021/104567
PCT Pub. Date: Jun. 3, 2021

(65) Prior Publication Data
US 2023/0131956 A1   Apr. 27, 2023

(30) Foreign Application Priority Data

Nov. 26, 2019 (DE) .......................... 102019131970.6
Mar. 11, 2020 (DE) .......................... 202020101350.5

(51) Int. Cl.
*A61F 5/56* (2006.01)
*A61N 2/06* (2006.01)

(52) U.S. Cl.
CPC ................ *A61F 5/566* (2013.01); *A61N 2/06* (2013.01)

(58) Field of Classification Search
CPC ........... A61F 5/0102; A61F 2005/0137; A61F 2005/0139; A61F 2005/0153; A61F 5/026;
(Continued)

(56) References Cited

U.S. PATENT DOCUMENTS 5,601,093 A    2/1997  Sheehan
9,808,371 B2 * 11/2017  Summer ................. A61F 5/566
(Continued)

FOREIGN PATENT DOCUMENTS

DE     19636680 C1     4/1998
DE     29822336 U1 *   3/1999   ............. A61F 5/566
(Continued)

OTHER PUBLICATIONS

Office Action mailed Jan. 20, 2022 in corresponding German Application No. 10 2019131970.6.
(Continued)

*Primary Examiner* — Tarla R Patel
(74) *Attorney, Agent, or Firm* — OSTROLENK FABER LLP

(57) ABSTRACT

The present invention is in the field of medical technology and relates to devices for preventing or alleviating snoring and apnea problems insofar as they can be attributed to what is known as snoring at the base of the tongue. In order to provide that they are easier and more comfortable to use and more effective than, for example, classic protrusion splints, but also do not cause the risk of a gag reflex, a connection system between the tongue and teeth is proposed that causes a retentive grab on the surface of the tongue by means of a rough surface facing the tongue, in particular by many small tips, which is characterized in that it contains a slide-on element for sliding onto several teeth on the left and right side of the upper jaw or the lower jaw, and comprises at least a respective one hook in its right- and left-sided molar areas or in its canine tooth areas, each for generating a form-fitting connection between the slide-on element and an undercut location on the respective row of teeth, with one such device being used in the upper jaw and one in the lower jaw, and permanent magnets located on the outside in housings (70)

(Continued)

attract each other and hold the tongue firmly in place. Ridges (100) arranged equidistantly on the housings (70) allow a freely selectable, comfortable protrusion of the lower jaw.

5 Claims, 5 Drawing Sheets

(58) Field of Classification Search
CPC .............. A61F 5/028; A61F 2210/009; A61F 2250/0067; A61F 2/0022; A61F 2/28; A61F 2/30; A61F 2/36; A61F 2/94; A61F 5/0125; A61F 5/055; A61F 2002/9528; A61F 2250/0004; A61F 2250/0065; A61F 2/013; A61F 2/14; A61F 2/82; A61F 2/95; A61F 5/013; A61F 9/007; A61F 9/00727; A61F 5/56; A61F 2005/563; A61F 5/566; A61F 5/58; Y10S 602/902; A61N 2/00; A61N 2/002; A61N 2/004; A61N 2/006; A61N 2/008; A61N 1/40; G09B 19/003; G09B 23/28; Y10T 29/49826
See application file for complete search history.

(56) References Cited

U.S. PATENT DOCUMENTS

| | | | |
|---|---|---|---|
| 2008/0199824 A1* | 8/2008 | Hargadon | ............... A61F 5/566 433/6 |
| 2012/0138071 A1 | 6/2012 | Summer | |
| 2013/0199542 A1* | 8/2013 | Summer | ........... A61M 16/0003 128/848 |
| 2014/0076332 A1 | 3/2014 | Luco | |

FOREIGN PATENT DOCUMENTS

| | | | | |
|---|---|---|---|---|
| DE | 102008041989 A1 | | 3/2010 | |
| DE | 102013100898 A1 | | 3/2014 | |
| EP | 2695589 A1 | * | 2/2014 | ............. A61F 5/566 |
| EP | 2882384 A1 | | 6/2015 | |
| KR | 20230070711 A | * | 5/2023 | ............. A61F 5/566 |
| WO | WO-2014127286 A1 | * | 8/2014 | ............. A61F 5/566 |

OTHER PUBLICATIONS

International Search Report mailed Feb. 16, 2021 in corresponding PCT International Application No. PCT/DE2020/100975.

\* cited by examiner

ANTI-SNORING DEVICE

STATE OF THE ART

The present invention is in the field of medical technology and relates to a device for preventing or alleviating snoring and apnea problems insofar as they can be attributed to what is known as snoring at the base of the tongue.

If an affected person sleeps on their back and lies on the back of their head, the entire base of the tongue moves downwards when the person sleeps relaxed and narrows the air passage in the back of the throat. This is known to lead to snoring noises. If the air passage is completely blocked, this leads to breathing pauses. Graphic illustrations for this phenomenon can be found in large numbers with a Google image search with the keywords snoring and cause, or for example under the following link: https://somnishop.com/prevent-snoring-what-can-you-do-against-snoring/

Surgery to remove or partially remove the uvula or other soft tissues in the throat to create space or to remove skin that is vibrating is expensive and, like any surgery, involves risk. They are associated with long-lasting pain during the healing phase and sometimes have little success if too little tissue is removed.

Numerous devices are known which address the problem mechanically by using some kind of equipment and do not require surgery. However, each individual device has individually identifiable disadvantages. Sleep masks for oxygen supply, for example, are complex and expensive, and putting them on is uncomfortable. If the person moves a lot while sleeping and the mask slips, it can lose all or part of its effectiveness.

Tooth splints can be individually adapted to the person by the dentist. They fix the lower jaw slightly forward relative to the upper jaw and thereby improve the passage of air through the pharynx, which is narrow in the supine position, which reduces snoring. However, they are often not effective enough, sometimes change the position of the bite and can lead to muscle pain in the jaw.

Other devices such as that from German patent DE 196 36 680 C1 or from utility model DE 298 22 336 U1 can trigger an unpleasant gag reflex and have individual parts that could be swallowed or that could accidentally get into the trachea.

The German patent application DE 10 2008 041 989 A1 discloses a lower jaw bite splint to which a band can be attached by means of hooks provided thereon. The band, in turn, can be connected to a piercing-like implant that can be attached to the top or bottom of the tongue. The implant has a button-like element that can be passed through a slit in said band, creating a connection between the tongue and teeth. The disadvantage of this is that the attachment between the button and the slot is a very tedious affair due to the narrowness in the oral cavity. This is true even when the button attached to the piercing is intended to be on the top of the tongue. When placed on the underside of the tongue, tying and untying the button-slot connection is even more difficult. However, for aesthetic and various other reasons, many people prefer to avoid being seen with a piercing in their mouth. For example, many older people who tend to snore because of their age do not consider a visible piercing to be serious enough if they are in a professionally responsible position.

The object of the present invention is to provide alternative devices for preventing or alleviating snoring and apnea problems which are easier and more comfortable to use relative to the approach of DE 10 2008 041 989 A1 and which, in comparison to the devices mentioned above, pose no risk cause a gag reflex and which are easier to handle and more comfortable than the classic protrusion splints available from dentists.

ADVANTAGES OF THE INVENTION

The objects according to the invention with the features of the independent claims solve this problem. Advantageous further developments and improvements of the respective subject matter of the invention can be found in the dependent claims.

The tongue is naturally difficult to grab. As is known in the art, the present invention is based on the solution that the tongue should be prevented from sliding down into the pharynx during sleep while lying on the back of the head in a supine position. It contains the general solution idea that the grab on the surface of the tongue can only be done by means of one or more larger "hooks" or "piercings", or with many small hooks or spikes, such as those found on a rough surface or on a brush.

According to a first aspect of the present invention, a device for alleviating snoring and apnea problems is disclosed having a connection system that connects the tongue to the teeth so that slippage of the tongue body into the pharyngeal area is reduced or avoided, the connection system providing a retaining grab on the surface of the tongue by means of a rough surface directed towards the tongue, in particular by many small peaks, which is characterized in that the connection system contains a slide-on element for sliding on several teeth of the left and right side of the upper jaw or the lower jaw, and the slide-on element in its right and left molar areas or in its canine areas contains at least one hook each for producing a positive connection between the push-on element and an undercut location on the row of teeth.

For use, the slide-on element on the upper jaw is hooked with its two hooks in suitable interdental gaps, for example between the first and second molars (between teeth 1.4 and 1.5 or 2.4 and 2.5), so that it has a reasonably tight fit. Then the user pushes his/her tongue forward while increasingly squeezing the tongue so that it is sandwiched between the palate of the upper jaw and the rough surface of the push-on element. The tips are preferably designed as gently acting, non-slip elevations and thus form the rough surface mentioned above. They lie on the same side of the push-on element as the hooks, see FIG. 10. They are preferably slightly inclined towards the incisors in order to enable the tongue to be pushed forward slightly and to prevent the tongue from slipping back too easily.

Variants of this also have pairs of magnets attached to the side, require two such push-on elements, which are also called "bite splints" or "connecting bodies", to enclose the tongue between these push-on elements and are described below and with reference to the other figures.

The present invention contains the further general idea that the grab on the surface of the tongue is held by a connecting body that is equipped with a certain number of relatively pointed elements that attach to the surface of the tongue, dig in there and get caught without to hurt the skin when these pointed elements act under some pressure on the tongue, wherein the connecting body also connects to a fixed part of the jaw or to several jaw parts right/left/top/bottom of the jaw.

In principle, the teeth, in particular the molars of the upper and lower jaw, are suitable as fixed jaw parts. Due to the connection system according to the invention, a large part of the tongue body is pulled up in the direction of the teeth or the chin against the force of gravity when the tongue body tends to slip down into the gullet and there to restrict the airflow. This pull on the body of the tongue greatly increases the free space in the throat, which is necessary for the passage of air. This reduces snoring or, depending on the anatomical conditions, prevents it entirely. In many cases, apnea states are completely prevented.

According to the above-mentioned approach of the invention, a connecting body for the detachable connection of the tongue with the teeth is disclosed, which preferably holds the tongue in relation to the teeth of the upper jaw and inhibits the movement of the tongue if the tongue tends to slip into the throat during relaxed sleep.

For this purpose, the connecting body, for which an exemplary embodiment is shown in FIGS. 1 and 2 comprises a support element for supporting the relatively pointed elements which are also denoted as anti-slip means further below, which can be present for example in form of a certain plurality—for example 14—of slightly flattened tips directed towards the surface of the tongue, which can preferably be formed in one piece with the support element.

Preferably, a support element with the tips acts on the upper side of the tongue and a second support element of a second connecting body, which can be constructed in the same way as the first connecting body, acts on the underside of the tongue. The device should be put in the mouth for use, with the tongue coming to rest with its front, freely movable area between the anti-slip means of both connecting bodies and being squeezed there between them, with the anti-slip means pressing a little into the flesh of the tongue without however, to injure the tongue. The tips preferably have such a shape and are present in an appropriate areal density that injuries or states of pain from "poking" at the tongue are avoided when a slight pressure via the squeezing force is exerted on the tongue lying between them.

The force required to squeeze the tongue is preferably achieved by the magnetic effect of attracting magnetically active elements. For this purpose, permanent magnets are provided in suitable receptacles on the support elements of both connecting bodies, preferably to the right and left of the tongue and outside of the dental arch, the permanent magnets interacting with suitably provided counterparts of the other connecting body and attracting each other as magnet-iron, or correctly oriented magnet-magnet—pair. They are arranged in pairs on the connecting bodies in such a way that the magnetically attractive parts can touch each other over as large an area as possible, either directly or separately through a thin housing wall of a housing in which they are housed, and establish an adhesive contact.

The housing can also be more or less open on various sides, but should hold the magnet or its counterpart firmly on the connecting body with a sufficient form fit.

The force required for squeezing the tongues can alternatively be produced in another suitable manner, in particular by means of snap fasteners or connecting elements which snap into one another and which are present on the two connecting bodies matching to one another.

At least one of the connecting bodies contains one or more hooks, preferably a hook for the right side and a hook for the left side of the upper jaw, which are designed in such a way that they can penetrate into an undercut location in the gap between two teeth in such a way that the hooks can apply the counterforce on the teeth which is necessary to keep the tongue from slipping down against its own weight.

In a simple variant, only the connecting body, which is associated with the upper jaw and the upper side of the tongue, provides the anchorage on the jaw, namely on the teeth of the upper jaw. In this case, the support element that squeezes the tongue on its underside is only magnetically attracted to the already anchored connecting body. In this case, the lower jaw is free, which can contribute to a relaxed sleep.

The connecting body for the lower jaw preferably also has a hook for hooking into the right row of teeth and a hook for hooking into the left row of teeth of the lower jaw. The lower jaw can also be brought into a protruded position relative to the upper jaw and held there in a comfortable way, which further reduces snoring.

The support element for the anti-slip means can be bent up or down, when it is web-shaped, made of the plastic PA12 and about 1 to 3 mm thick, which can be advantageous when inserting or removing the device from the mouth, because when bending the support element the distance between the tips of the hooks will change.

The magnetically effective elements mentioned above are preferably made from neodymium alloys and are constructed and dimensioned in such a way that they interfere as little as possible in the mouth.

The support element with the anti-slip tips preferably spans the free space between the front molars of the left and right rows of teeth in the upper jaw and in the lower jaw. For example, the hooks sit in the gap at the undercut location between the first and second molars on the left and right rows of teeth of the upper jaw. If the supporting element for the underside of the tongue is also to be hooked into the lower jaw, it is advisable to ensure a slight protrusion by anchoring the hooks between the second and third molars. The lower jaw is then held in a slightly protruded position when it comes into contact with the magnetic counterparts on the support element of the upper jaw. The special advantage, however, is that the degree of protrusion can always be varied by the user, which is particularly advantageous when the jaw hurts because of the protrusion. The user can then return to a normal position of the jaws in relation to one another, preferably in a stepwise variation, see below for details. But the tongue is still prevented from sliding down the gullet. This is a particular advantage over prior art protrusion splints.

The hooks can also be anchored to interdental spaces other than those mentioned, with or without protrusion, and if desired or anatomically there is no other way, also in the left half of the jaw in a different way than in the right.

The magnetically effective parts are preferably built flat and cuboidel. They can preferably each be accommodated in a suitable housing, which in turn can be designed in one piece with the support element if it is to be produced by injection molding or by 3D printing. However, the magnetically effective parts can also be glued to the device, for example by means of a suitable adhesive, such as is commonly used in dental practices. The housing or the magnetically active parts are preferably not seated on the dental arch but rather on the side and outside of the dental arch. Then the tongue has relatively space and can be squeezed gently over a large area.

If the permanent magnet and counterpart exert direct adhesive contact or adhesive contact via the housing surfaces between them, the lower jaw is actually fixed relative to the upper jaw, but in a way that allows easy and comfortable release of the fixation, such as when speaking, or when the jaw muscles should hurt, which is a great improvement over the prior art. Depending on the roughness of the adhering adhesive contact surfaces and the strength of the magnetic attraction force, the lower jaw can be displaced more or less easily relative to the upper jaw. The adhesive contact surfaces on the housings of the magnets or the counterparts—or the magnets and their counterparts themselves—preferably have a corresponding pattern of ridges of the same shape, which are formed in terms of shape and arrangement in such a way that the ridges of the four housings (two of the device on the upper jaw and two of the device on the lower jaw) can hook into one another in several different positions of the housings.

The ridges can preferably also have a certain curved shape, so that they still fit together when the adhesive contact surfaces are slightly twisted relative to one another, which can also be necessary given the individual rounded shapes of the jaw arches of different people.

In order to achieve a large attraction, the distance between the magnet and its counterpart can be reduced. For this purpose, the ridges mentioned can be made so long that they run from wall to wall and completely cover the housing. Then the cover of the housing that actually runs under the ridges, which is also referred to here and in the figures by the term "adhesive contact surface 80", can also be omitted. A new surface for the adhesive contact between two housings is then formed between the ridges and the housing walls. The housing can then also be built correspondingly flatter.

As a result, the connection system according to the invention has a double effect: firstly by preventing the lower jaw from sliding down relative to the upper jaw when the person is sleeping relaxed on the back of the head, and secondly by keeping the tongue in a higher position relative to the upper jaw. Both effects reduce snoring in a recognized manner and add up to an improved overall effect against snoring problems without the person having to put up with serious disadvantages.

Another advantage is that the teeth no longer touch, even if the person makes chewing movements during sleep and is prone to grinding and bruxism. Therefore, the device according to the invention is in principle also suitable for people suffering from bruxism.

For an average dentition anatomy, the device according to the invention does not require any individual adaptation to the personal dentition, because they can hook into an undercut zone in a gap between two molars with a pointed hook or a pair of opposite such hooks in the right molar area and the same arrangement in the left molar area. Such undercut zones are very common in the molar area. Very often in adults there are even 0.2 mm to 0.8 mm wide and 0.5 mm to 3 mm high passages between the gums and a more or less closed joint between two teeth in the molar area as a useful undercut zone for hooking.

As a material for the device according to the invention the often for bite splints used PMMA or the somewhat less brittle plastic usually used for dental floss sticks, can be used, if the connecting bodies are to be produced by injection molding. Harder, thermoplastic elastomers are also suitable. Polyurethane, polypropylene, ABS are other plastics that are suitable in principle. The plastic PA12 is particularly suitable for 3D-printing, since the tips and the hooks, which are actually quite thin, do not break so easily during use. Depending on the modulus of elasticity and breaking strength of the material, the shape of the hook should be strong enough so that it does not break off when the splint is inserted or removed. The hook can also be made only slightly flexible if the support element as a whole is somewhat flexible, so that the two end areas of the support element with the hook can be flexibly pushed apart somewhat when inserted, thereby increasing the distance between the hook ends and the hooks then slide into the undercut zones when released. If a material is not biocompatible enough, it can still be used if its surface is coated with a biocompatible lacquer.

According to a further solution idea of the invention, a slide-on element is disclosed for sliding onto one or more teeth of the lower jaw and one for sliding onto one or more teeth of the upper jaw to produce a connection system which connects the tongue to the teeth and holds them between the teeth without slipping away when the tongue is pushed to a certain extent—preferably with its front part—between the two rows of teeth of the upper and lower jaw and at least a slight pressure is exerted from the rows of teeth over the rough or spiked surface of the push-on element on the upper and lower Tongue surface, so that sliding of the tongue body into the pharynx can be reduced or avoided.

The slide-on element has a tongue-facing surface that is rough, or has a certain multiplicity of short spikes—from, for example, one to ten spikes per square centimeter—or is provided with very short bristles, which rests in contact with and under slight pressure on the tongue surface with the many small tips or bristles, depending on their shape and contact pressure, slightly hooks into the surface of the tongue and thus causes the tongue to be non-slip, which prevents the tongue from slipping into the gullet while sleeping on the back. The user prefers to use one slide-on element for the row of teeth in the lower jaw and at the same time one for the row of teeth in the upper jaw. A push-on element preferably covers the incisors and the canine area, depending on the situation also the front and central molar area. The surface effective for "squeezing" the tongue extends along the curved longitudinal extent of the push-on element with a width of preferably 5 mm to 20 mm.

The tips are preferably of such a shape and are of sufficient areal density to avoid injury or pain from "poking" the tongue when slight pressure is applied through the jaws to the intervening tongue.

According to a particularly preferred embodiment, a permanent magnet is arranged on one bite splint and a magnetically attractable counterpart on the other bite splint so that they are exactly opposite when the bite splints have been slid onto their respective row of teeth to fit. The bite splints thus tighten slightly, which further supports the pressure on the tongue, even when the jaw muscles are relaxed. When the permanent magnet and counterpart are in adhesive contact, the lower jaw is actually fixed relative to the upper jaw, but in a way that allows easy and comfortable release of the fixation, such as is required when speaking, which represents a real improvement over the prior art. As a result, this connection system has a double effect: firstly by preventing the lower jaw from sliding down relative to the upper jaw when the person is sleeping relaxed on the back of the head, and secondly by keeping the tongue in a higher position relative to the upper jaw. Both effects reduce snoring in a recognized manner and add up to an improved overall effect against snoring problems without the person having to put up with serious disadvantages.

In a special variant of this, the bite splints do not require any individual adjustment to the personal dentition, because they can hook into an undercut zone in a gap between two molars with a pointed hook or a pair of opposite such hooks in the right molar area and the same arrangement in the left molar area. Such undercut zones are very common in the molar area. Very often in adults there are even 0.2 mm to 0.8 mm wide and 0.5 mm to 1 mm high passages between the gums and a more or less closed joint between two teeth in the molar area as a useful undercut zone for hooking.

The distance between the hooks or the pair of hooks and the inner cheek of the bite splint in the area of the incisors is small enough so that the bite splint fits loosely into the dental arch when hooked in without touching the inner flanks of the incisors. The inner cheek of the bite splint only has a stabilizing effect. With a suitable choice of material and material thickness of the bite splint, it can also be omitted entirely, which further increases the universal adaptability of the bite splint and contributes to the fact that the splint with its end pieces on the molars can be bent up or down more easily, which can be advantageous, when inserting or removing the splint from the mouth, as is described in more detail further below.

The bite area on the occlusal surface is wide enough so that the incisors can still reach it and the tongue can be clamped between the incisors if necessary. The pair of bite splints can thus be made in three standard sizes "small", "medium" and "large" and therefore fits almost all adults.

PMMA, which is often used for bite splints, or the somewhat less brittle plastic commonly used with dental floss sticks, can be used as the material for the bite splints if the bite splints are to be produced by injection molding. Harder, thermoplastic elastomers are also suitable. Polyurethane, polypropylene, ABS are other plastics that are suitable. Depending on the modulus of elasticity and breaking strength of the material, the shape of the hook should be strong enough so that it does not break off when the splint is inserted or removed. The hook can also be slightly flexible if the bite splint is slightly flexible as a whole or only slightly in the incisor area, so that the two molar areas can be flexibly pushed apart when inserted and the hooks then slide into the undercut zones when released. The plastic PA2200 is particularly suitable due to its certified biocompatibility.

The strong magnets made of neodymium alloys mentioned above, preferably with a gold coating, are particularly suitable.

DRAWINGS

Embodiments of the invention are shown in the drawings and explained in more detail in the following description.

DESCRIPTION OF THE EXEMPLARY EMBODIMENTS

In the figures, the same reference symbols denote the same components or components with the same function.

Figure 1:
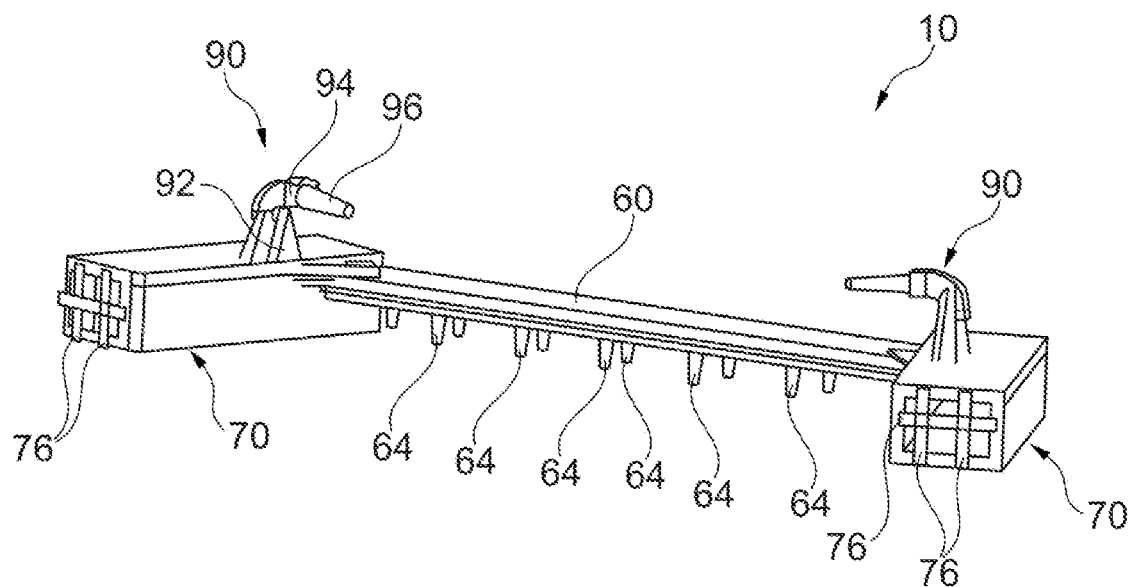
FIG. 1 shows an exemplary embodiment in a perspective view obliquely from rear and above, as it can be inserted in the upper jaw.

FIG. 1 shows an exemplary embodiment of a connecting body 10 according to the invention in perspective from above at an angle, as it can be used in the upper jaw.

Figure 2:
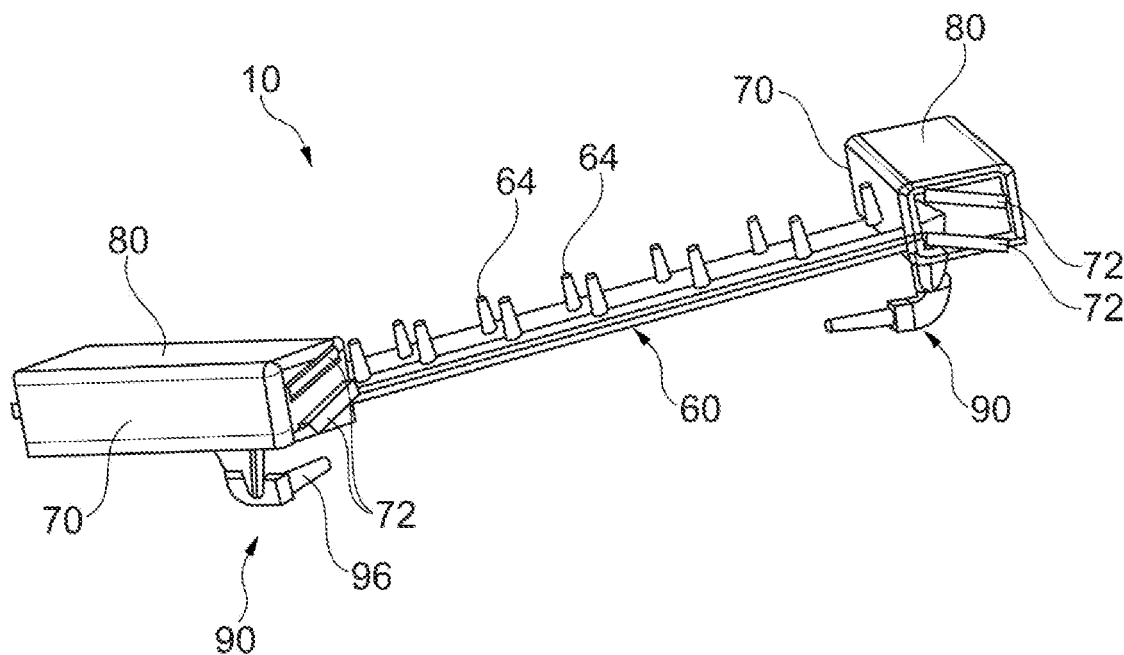
FIG. 2 shows the same part as shown in FIG. 1, but obliquely from the front and above, which can be inserted in the lower jaw.

FIG. 2 shows the same connecting body as shown in FIG. 1, only obliquely from the front and above, which can be inserted into the lower jaw.

The connecting body 10 according to the exemplary embodiment consists of a flexible, hard plastic, in the example made of the plastic PA12, which is suitable for 3D printing processes and is biocompatible. It is designed with sufficient space for the teeth of the upper and lower jaw, so that no individual adjustment to the personal dentition is necessary. According to the invention, the above-mentioned tips 64 are already worked into the material by the manufacturer. The tips 64 are present in an appropriate number and areal density on the surface of the rail facing the tongue, in the example 13 pieces on an approximately cuboid support element of approximately 4 cm in length, 8 mm in width and 1.4 mm in thickness. The basic shape of the tips is preferably conical or pyramidal or cylindrical. The height in the example is about 3 mm. The opening angle at the tip is about 15°. Depending on the hardness of the material used and the number of tips per unit area, the free height of the tips 64 above the surface of the support element should be adjusted so that the tongue does not cause any pain under slight pressure, but the tongue is still prevented from slipping away. The tips 64 are therefore not needle-sharp, but flattened to avoid pain or injury, but with a relatively edgy end to effectively prevent the tongue from slipping off.

According to the exemplary embodiment, a permanent magnet is now preferably provided on both end sections of the support element 60 in a cuboid, hollow housing 70 with a wall thickness of approximately 0.7 mm. After the device has been inserted into the mouth, the housing 70 sits laterally outside the row of teeth in the direction of the cheek in the molar area. Corresponding to an average shape of the outer contour of a row of teeth in human teeth, it is arranged slightly obliquely and approximately adapted to the outer contour of the row of teeth. It is formed in one piece with the support element 60 and the hook 90, described below, for anchoring the device in the row of teeth.

The permanent magnet or its magnetically attractable counterpart is 20 mm long, 5 mm wide and 1 mm thick and can be placed in the housing 70 after 3D printing or casting the device as shown in FIG. 1 or 2. For this purpose, on the open first end face of the housing facing the lip (during use), two closure webs 72 are connected to the edges of the housing, which are oriented approximately parallel to one another and at a clear angle relative to the contact surface of the housing. Their distance from each other is so large that the magnet or its counterpart can be pushed through with a little effort. The other open face of the cuboid, which is directed towards the throat when the user is lying on his back, is closed in the manner of a grid by transverse and longitudinal webs 76 with a grid size which is in any case smaller than the magnets to be inserted or their counterparts. Therefore, there is no risk that they leave their housing and unintentionally get into the pharynx.

The housings 70 have an internal height of 2.6 mm, so that, if necessary, two magnetically active cuboids can be arranged one above the other instead of just one, in order to be able to strengthen the magnetic force if necessary.

To use the device, a cuboid permanent magnet is first placed in each of the two housings 70 of the device for the upper jaw shown in FIG. The permanent magnet is made of an alloy containing neodymium. To insert it, it is held at an angle and pushed through the slot between the two locking bars.

In the device according to FIG. 2, which is manufactured identically to that of FIG. 1, two magnetically attractable counterparts, for example made of ferromagnetic iron, are used, which have essentially the same shape and size as the permanent magnets. Alternatively, similar permanent magnets are inserted in the correct orientation so that the connecting bodies attract when inserted in the mouth, see FIGS. 3 and 4.

Figure 4:
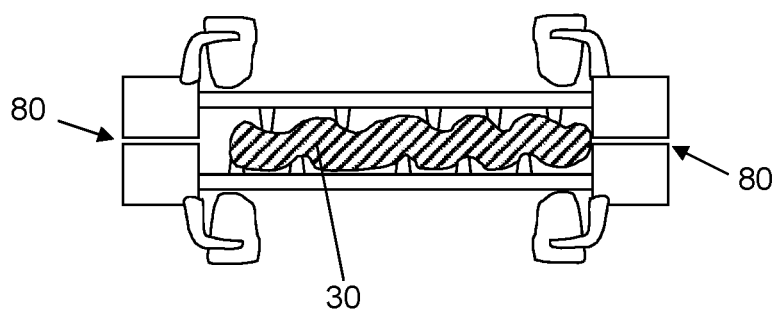
FIG. 4 shows the device of FIG. 3 after the devices have been approached to each other by slowly closing the mouth with the tongue interposed, the tongue being shown for better understanding in a cross-sectional view in a plane spaced about 1 mm from the row of tips in the direction to the lips.

In use of the device, it is preferred that the facing surfaces 80 of the four housings 70 touch in pairs, as shown in FIG. 4. The magnets and their counterparts rest with their flat, 5 mm wide and 20 mm long surfaces on the inner surface of the respective housing, which is only slightly larger. The associated outer surfaces of the housings form the adhesive contact with one another. They are therefore called "contact surfaces" 80 herein. The magnetic force of attraction acting in pairs is so high that, despite being shielded by the approximately 0.8 mm thick housing surfaces 80 on both sides, they exert such a strong force of attraction on one another that the tongue, when it is inserted between the anti-slip tips, is clamped there sufficiently firmly. Experiments have shown this. The height of the peaks 64, which is preferably designed to be the same throughout, relative to the level of the contact surfaces 80, should be set in such a way that the peaks are at most 1 mm below this level. This is suitable for most people if the tongue is to be pinched in the stable adhesive contact of the contact surfaces 80. If the tongue needs a little more space, the user can carefully file down the tips slightly. Constant adhesive contact helps to relax the jaw muscles.

In normal use, the magnets and their counterparts will remain lodged in the housings and will not fall out through the face facing the lips, even if the spacing of the closure webs 72 should be slightly excessive due to acceptable manufacturing tolerances, as there is always a certain attraction between the magnetically effective cuboids, which means that they always align themselves parallel to each other. Due to this parallelism, they are additionally prevented from leaving the housing by the obliquely sloping closure webs 72. However, a magnetically active cuboid that has gotten out of its housing through grossly improper use will not get into the throat because it is automatically drawn in the mouth of the sleeping person to one of the other cuboids that attract it. The risk of choking during sleep is therefore negligible.

Hooks 90 are attached with their shank 92 to the side of the housing 70 opposite the contact surface 80. The shank 92 has a relatively large contact area with the housing and is stably attached to the housing during manufacture by injection molding or 3D printing. The shank 92 ends conically in a curved piece 94, which curves about 90° inwards towards the row of teeth. The curved piece 94 then transitions into a straight tip, which has a length of about 5 mm and has a slightly conical shape, which tapers further and further to a slightly rounded tip of about 0.5 mm. This allows the tip to be inserted in most people into the common interdental spaces between two molars. As a result, the connecting body is anchored to the upper jaw or lower jaw and can counteract the weight of the tongue, which slips away downwards during a relaxed sleep, with a sufficiently large counterforce, so that the tongue can be reliably held in the front of the mouth in its status pressed between the two supporting elements by the many small points present there. The hook is preferably made in one piece with the support element for the anti-slip means by injection molding or 3D printing and is flexible to a certain extent.

Advantageously, due to their construction principle, the connecting bodies according to the invention do not require any individual adjustment by the dentist, but can be used at least by most adults without individual adjustment.

Figure 3:
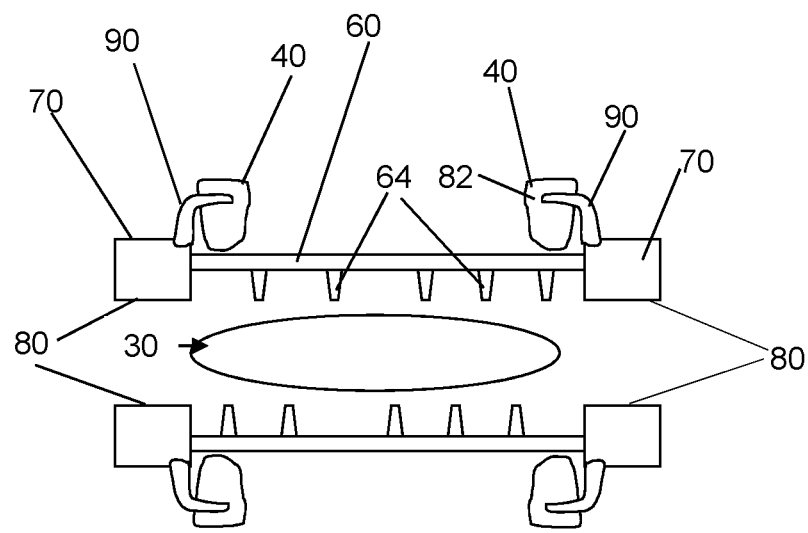
FIG. 3 shows the device from FIGS. 1 and 2 anchored in an undercut location in an interdental space of the row of teeth of the upper jaw or lower jaw as a schematic view drawing with the omission of the other teeth, with a tongue placed between them, and with a certain vertical distance from one another, so that the tongue is not squeezed.

FIG. 3 shows the device from FIGS. 1 and 2 from the front in a schematic and simplified form anchored in an undercut location in an interdental space of the row of teeth of the upper jaw or lower jaw as a schematic view drawing with the omission of the other teeth, with an interposed tongue 30, and with some vertical distance to each other so that the tongue is not pinched.

FIG. 4 shows the device of FIG. 3 after the devices have been brought together with the tongue 30 interposed, by slowly closing the mouth until adhesive contact is made at the contact surfaces 80, the tongue being shown for better understanding in a cross-sectional view in a plane approximately 1 mm spaced from the row of peaks in direction to the lips.

Referring to FIGS. 3 and 4 together, only one tooth 40 per quadrant is shown in simplified form, intended to represent the position of the tip of the hook at the undercut location between the equator of the molar and the gum.

The tip of the tongue is located further forward in the direction of the incisors or, depending on the individual bite, can also be pushed between the incisors in order to move the tongue body as a whole further away from the throat. An intense snorer can therefore stretch the tongue as far forward as possible and squeeze it in that position.

The partially squeezed tongue 30 shown hatched in FIG. 4 is preferably held at so many tips 64 that the engagement of the tips does not cause any significant pain. It is advisable to arrange the tips 64 in two rows offset from one another so that they are not arranged on top of each other.

A positive side effect is that the teeth no longer touch, even if the person makes chewing movements during sleep and tends to grind their teeth and bruxism. Therefore, the device according to the invention is also suitable for people suffering from bruxism.

As can also be derived from FIG. 4, it is sufficient for a person with only a moderate tendency to snore if only the device for the upper jaw is anchored in his row of teeth by means of hooks on the right and left and the device for the lower jaw only clamps the tongue, while not being anchored in the lower jaw.

The support element 60 for the anti-slip tips 64, together with the two housings 70 and the two hooks 90, preferably forms a stable, one-piece workpiece.

Figure 5:
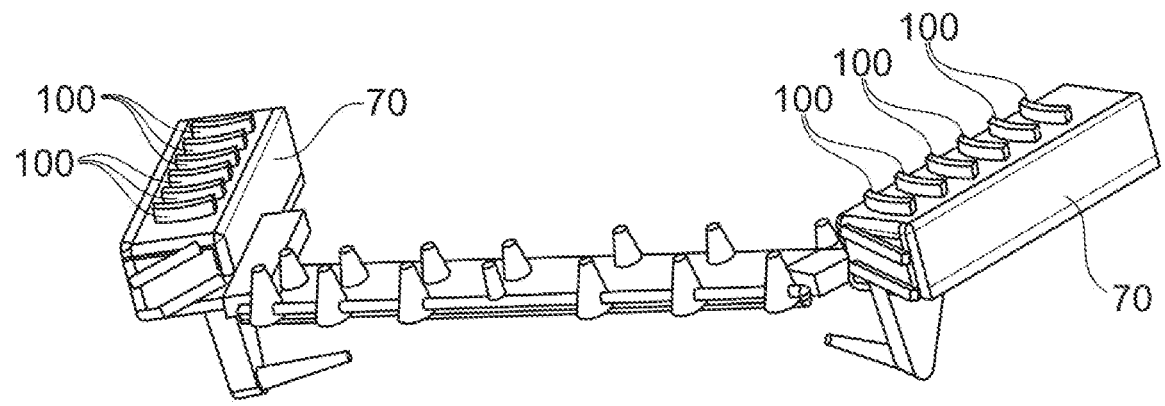
FIG. 5 shows a further embodiment in which the housings are arranged further back and the adhesive contact surface of the housings is provided with curved ridges.

FIG. 5 shows a further exemplary embodiment in which the housings 70 are arranged further back and the adhesive contact surface 80 of the housings 70 is provided with curved ridges 100.

Figure 6:
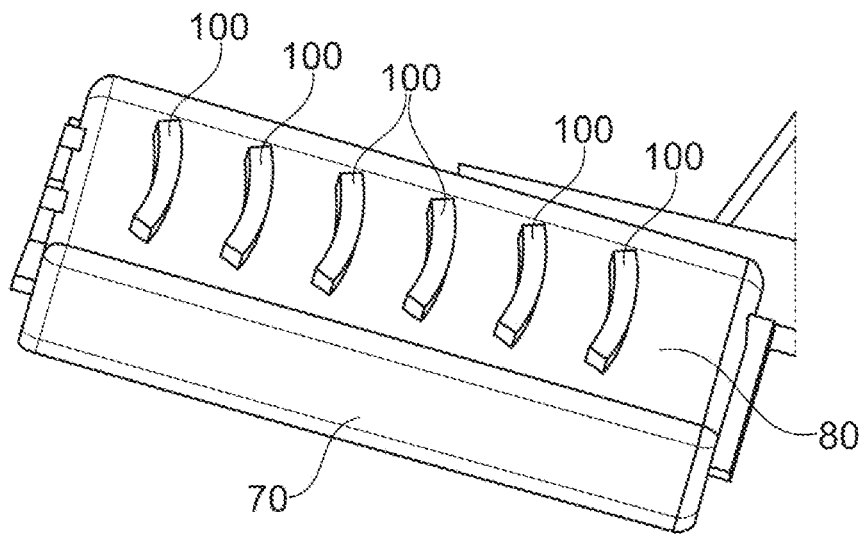
FIG. 6 shows a section of the housing shown on the left in FIG. 5, viewed obliquely from the side and above.

FIG. 6 shows a section of the housing 70 shown on the left in FIG. 5, viewed obliquely from the side and above.

With common reference to FIGS. 5 and 6, the ridges are formed integrally with the housing 70 by 3D printing. The ridges are edge sections of an approx. 40° segment of a circular edge. They have a rectangular cross section with a width of about 0.7 mm and a height of about 0.8 mm. In the example shown, they extend over approximately two-thirds of the width of the housing contact surface 80 and are always arranged with the same shape in a pattern of parallel ridges, with a clearance between them of approximately 2.5 mm. The pattern of the housing shown on the left is arranged somewhat offset in relation to the pattern of the housing shown on the right, so that the ridges 100 of two such devices from FIG. 5, which are identical in shape, come to lie one inside the other when one is hooked into the upper jaw and the other into the lower jaw and the adhesive contact surfaces 80 overlap at most. If the user now wants to alleviate the protruded position a little and would like to set less protrusion, he only briefly lifts the lower jaw out of the adhesive contact so that the ridges no longer touch each other when the lower jaw is pushed back, then pushes the lower jaw into a slightly less protruded position and locks the ridges in the new position by relaxing and thus automatically restoring the magnetically effected adhesive contact. So, this allows the user to vary the degree of protrusion. In the example shown, there are around 7 possible variations, with the housing still overlapping sufficiently to generate sufficient attraction between the two devices in the upper and lower jaw.

A particularly simple and cost-saving embodiment results from the fact that the two devices for the upper and lower jaw are produced in exactly the same way using the same set of molds or the same 3D print data. The hooks can then be anchored in the lower jaw area, which in most people has a slightly smaller dental arch than in the upper jaw, for example between the 2nd and 3rd molars, and in the upper jaw between the first and second molars. As a result, a certain protrusion of the lower jaw is usually automatically achieved when the mouth is closed, which additionally reduces snoring.

If a person has a slightly smaller denture than average, they he can usually still use the connecting bodies because they preferably only have one hook per quadrant of the jaw. Then, to get a tight fit, the person with the smaller arch can hook the appliances further back in the jaw.

Another great advantage compared to the classic protrusion splints is that the connecting body for the lower jaw can be gradually shifted by a few millimeters relative to the connecting body on the upper jaw while wearing it, depending on need and depending on the occurrence of jaw pain, without it must be completely taken out of the mouth. This results in an individual adjustment option that is not available with many other classic protrusion splints.

Figure 7:
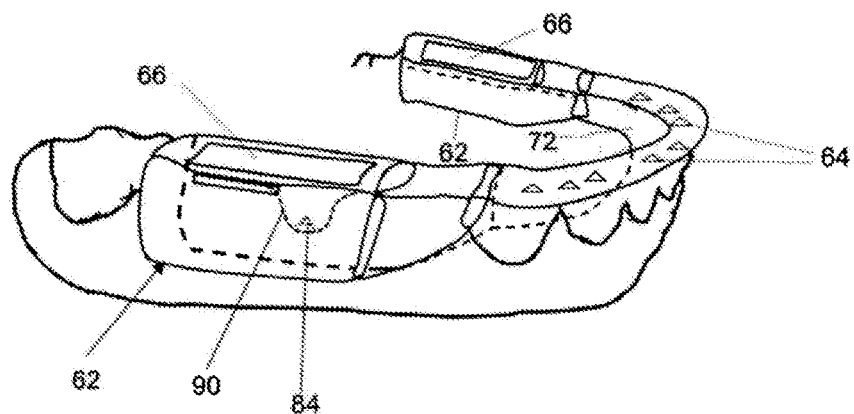
FIG. 7 shows an embodiment of a bite splint as a push-on element for the lower jaw, in which only the molar area is surrounded by the splint, the canine and incisor area has only one supporting cheek along the dental arch on the inside of the mouth, and the anti-slip surface is adjacent to the supporting cheek, and the outer stringer is not present.

FIG. 7 shows an embodiment of a bite splint as a push-on element 62 for the lower jaw, in which only the molar area is tightly surrounded by the splint with an inner cheek and an outer cheek, so that the magnetic tensile forces are transferred to the jaw.

The magnetically active parts 66 are connected to the bite splint by being glued to the surface of the splint with an adhesive or a suitable dental cement. In a variation, the magnetically active parts 66 can be connected to the bite splint by means of a form-fitting connection, in that they can be inserted through an opening into a cavity with a format that matches the magnetically active parts, which is located parallel to the bite plane, so to speak, on the occlusal surface, and forms a kind of "Bag"—see also the description of FIG. 9. The canine and incisor area has only one inner cheek 72 as a support and stabilizing element along the dental arch on the inside of the mouth, which is somewhat shortened relative to the inner cheek in the molar area and is connected to it in one piece. The anti-slip surface with the tips 64 connects integrally with it to the inner cheek 72 as in the example of FIG. 8. The outer cheek in the incisor area is not present, which results in a easier wear feeling, which gives some flexibility to the bite splint, which may be helpful when inserting the splint which and looks more aesthetic because the lips are not pushed outward. The slight pressure on the tongue can still be applied adequately despite the absence of the outer cheek.

A matching push-on element can be produced analogously for the upper jaw. The bite splints can be applied in such a way that the upper jaw splint is inserted first and then the lower jaw splint, or vice versa. The rails can also be removed again.

This results in a comfortably portable device that prevents the lower jaw from moving towards the pharynx, while the tongue is again independently pulled away from the pharynx with the same device. In order to further increase user comfort, the inner cheek in the incisor area can also be omitted entirely.

Another great advantage compared to the classic protrusion splints is that the lower jaw splint can be gradually shifted a few millimeters against the upper jaw splint while wearing it, depending on need and depending on the occurrence of jaw pain, without the splint having to be completely removed from the mouth. This results in an individual adjustment option that is not available with many other classic protrusion splints.

Figure 8:
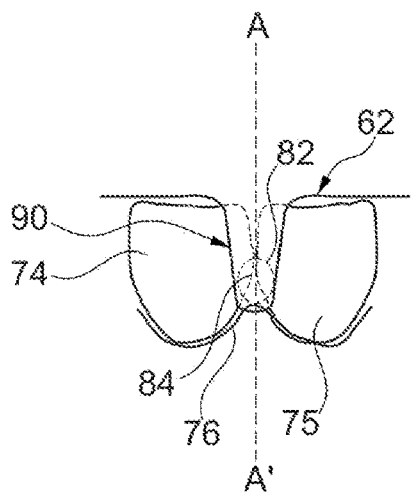
FIG. 8 shows a side view from the outside to a tooth gap in the molar area of a lower jaw, a hook lying in front of the gap of a bite splint, which is only partially shown.

FIG. 8 shows a side view of a tooth gap in the molar area of a lower jaw seen from the outside, a hook 90 lying in front of the gap of a bite splint 62 shown only partially according to a further embodiment of the present invention.

Figure 9:
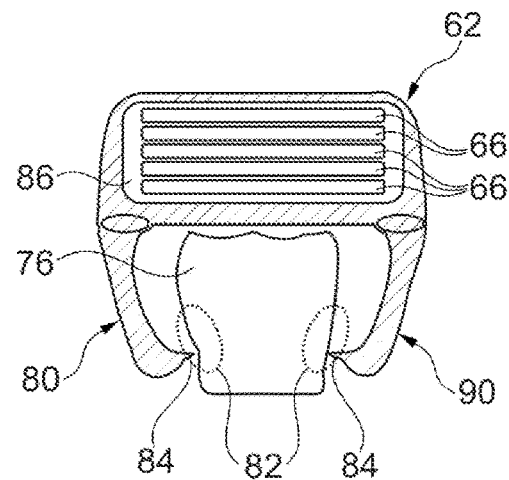
FIG. 9 shows an exposed sectional representation along a line AA' from FIG. 8 of the tooth gap from FIG. 8, from the perspective of an adjacent tooth, with a pair of hooks of a bite splint that is only partially represented.

FIG. 9 shows an exposed sectional view along a line AA' from FIG. 8 on the tooth 74 from FIG. 8, from the perspective of an adjacent tooth 75, with a pair of hooks of a bite splint 62 only partially shown, wherein both hooks hook with their tips 84 in an undercut location 82 at a tooth gap between two molars and with a pocket worked into the bite splint in one piece to accommodate five plate-shaped permanent magnets 66 arranged one above the other.

With common reference to FIGS. 8 and 9, a bite splint 62 for the lower jaw and a bite splint 63 for the upper jaw are provided, which each contain one or more permanent magnets 66 or a magnetically attractable counterpart 70 at the molar tooth-sided end section, wherein the bite splints are designed such that an individual adaptation to the dentition of the person using it is not necessary in most cases.

In order to achieve that both bite splints do not require an individual adjustment by the dentist for sitting firmly on the rows of teeth in the molar area, two opposite, slightly flexible hooks 90 are provided to create a positive connection between the bite splint and an undercut location 82 on the row of teeth. Such undercut locations are often found in the molar region of humans at the bottom of the gap between two molars or at the bottom of the gap between the canine and the molar. The flexurally elastic hooks 90 have two opposing tips 84 at their ends, which point toward one another. They are under a certain pretension, so that the tips 84 penetrate into the tooth gap from both sides when the bite splint is pushed onto the row of teeth from above. When the bite splint is correctly placed and pushed onto the row of teeth of the molars, the flexible hooks 90 each yield somewhat, as a result of which the tips 84 initially diverge. This allows the splint to be pressed further onto the row of teeth, with the tips 84 of the hooks sliding on the edge of the gap between two teeth 74, 75 in the direction of the gums 76 until they snap into the "hole" of the undercut location 82 at the bottom of the tooth gap, because they are under an appropriately set preload. This gives the bite splint a sufficiently tight fit on its row of teeth in order to withstand the magnetic attraction force of the corresponding magnetically active parts 66, 70 and to transmit the magnetic force to the upper and lower jaw.

The opposing hooks 90 can be produced in one piece with the bite splint by means of molding or 3D printing and are preferably placed on the bite splint in such a way that they can snap into the tooth gap between the second and third molars. In one variant, they are placed so that they can snap between the first and second molars.

The permanent magnets 66 and their counterparts 70 are bonded to the respective bite splint by a biocompatible adhesive or dental cement. Alternatively, they can be attached to the respective bite splint in a form-fitting connection by pushing them into a pocket 86 before use, as explained above in FIG. 7 or below in FIG. 9.

The universally fitting bite splints according to the exemplary embodiment in FIGS. 8 and 9 can have less material on the lateral inner and outer cheeks, since they build up the necessary clamping force on their row of teeth with less surface—just the surface of the hooks 90. The hook 90 with its tip 84 is drawn in dashed lines in FIG. 7 with respect to the outer cheek in the molar region for comparison with the exemplary embodiment from FIG. 7. This has the advantage of being more comfortable to wear, because there is less foreign matter mass in the mouth.

In a preferred variant of the exemplary embodiment of the universally fitting bite splint, the hooks 90 are only present on the outer cheek in the molar area and the bite splint is produced in the incisor area without an inner cheek or only with a very short inner cheek, in such a way that it can be bent somewhat flexibly up and down. As a result, when inserting them, it can be bent open slightly with two hands gripped between the thumb and forefinger, as a result of which the hooks 90 can be easily slipped over the row of molars on the left and right. When released, the bite splint is pretensioned and the hooks 90 catch in the undercut location 82. To release the bite splint, the steps are carried out in reverse order. Alternatively, the user can slide a stick of dental floss between the row of teeth and the splint and pry the hook 90 out of the undercut location.

With well thought-out dimensioning of the universally fitting bite splint, one and the same bite splint of a certain size "small", "medium" or "large" fits for the lower jaw and for the upper jaw. This has the advantages of even lower production costs and increased convenience of use because the user cannot mix up the splints.

The recess referred to as a "pocket" in the various variants of the bite splint according to the invention can also have a slit, preferably a longitudinal slit in the direction of the insertion opening for the magnetically active parts, through which a thin rod, such as a dental floss stick, can be inserted and the magnets 66 or its counterpart 70 can be pushed out of the pocket again. The slit can also be deliberately widened in order to reduce the magnetic force as little as possible through the material of the bite splint.

In a further exemplary embodiment, a protrusion splint is disclosed according to the previous description of FIGS. 7 to 9, but in which no anti-slip surface is provided for clamping the tongue, but only a permanent magnet with a counterpart in the molar area on the right and left is provided, but nothing else mechanical "interlocking" of the two tooth splints is provided. The above-mentioned gradual displacement option for spontaneous pain relief can also be achieved with this.

Figure 10:
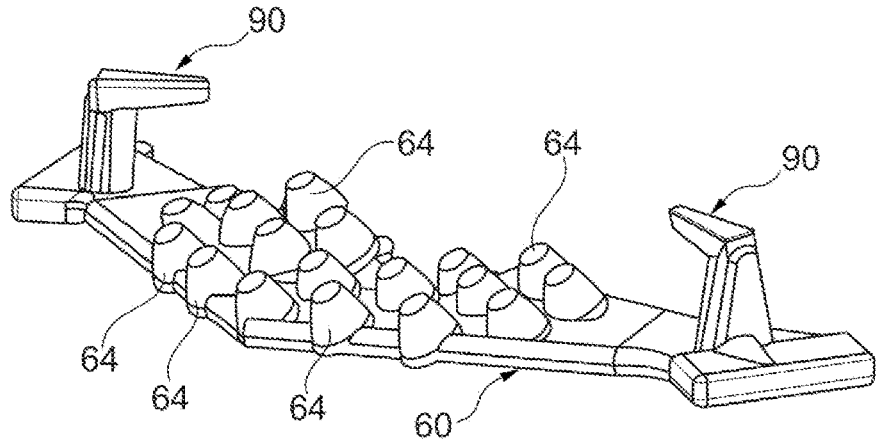
FIG. 10 shows a further exemplary embodiment which does not require permanent magnets and in which the "rough" surface of the connection system between tongue and teeth provided with points points in the same direction in which the hooks extend.

FIG. 10 shows another embodiment in which the "rough" surface of the connection system between the tongue and teeth, provided with somewhat rounded tips 64, points in the same direction in which the hooks extend.

The connection system again contains a slide-on element for sliding onto and hooking into the row of teeth on both sides, which also serves as a support element 60 for the tips 64, as described above. When used in the upper jaw as shown, it extends from the left to the right row of teeth in the same half of the jaw, for example from the left molar row across to the right molar row in the upper jaw. It can be anchored there with the aforementioned hooks 90 in an undercut location on the right and left coming from the outside in the respective molar area, as described above. The gently formed peaks 64, which determine the roughness of the surface, are now arranged on the opposite flat side of the support element 60 compared to FIG. 1.

The gentle tips 64 are directed slightly toward the incisors to create a slight "barb action" against the surface of the tongue to further inhibit slippage of the tongue toward the throat. In this way, a particularly advantageous non-slip surface is formed.

For use in the upper jaw, the user hooks the device with the hooks 90 on the right and left into suitable tooth gaps in the molar area of the upper jaw. If he has a narrow jaw, he hooks the device further back because the dental arch is wider there. If he has a very wide jaw, he hooks it in further forward. Unsymmetric hooking also works. The non-slip surface thus stretches from left to right in the molar area of the upper jaw and is directed upwards. Then the user pushes his tongue into the narrow, free space between the palate of the upper jaw and the non-slip surface. The underside of the tongue comes into contact with the tips 64 on the non-slip surface. Since the tongue is normally thinner at the tip and thicker toward the back, the further it is pushed forward, the tongue lies more and more tightly between the palate surface and the non-slip surface when pushed forward. The palate and the non-slip surface exert increasing pressure on the tongue. For this purpose, the hooks 90 form the abutment lying in their respective undercut location of the row of teeth.

At some point when pushing forward, a "fixing point" is reached at which the tongue no longer slips back on its own due to the then sufficient pressure of the non-slip surface of the support element 60 when the user relaxes and lies on his back, as it is during sleep the case. Since the cross-sectional area of the tongue and its course from the tip of the tongue backwards is individually different for each person, and this also applies to the curvature of the upper jaw palate, this "fixing point" is also individual.

For this reason, the support element 60 is not made too deep, so that there is a free space between its front edge and the incisors, through which the tip of the tongue can push if it is necessary, for example for users with a narrow and thin, rather elongated tongue. The tongue can then be pushed further and further forward and, if necessary, rolls down again on the inner flanks of the incisors. In this way, a long, thin tongue can be held far back and frees the throat for snoring-free breathing.

In this basic version of the connection system according to the invention, the push-on element does not require permanent magnets on the sides and also no second push-on element if the user accepts that his lower jaw will fall back slightly when sleeping on his back.

Figure 11:
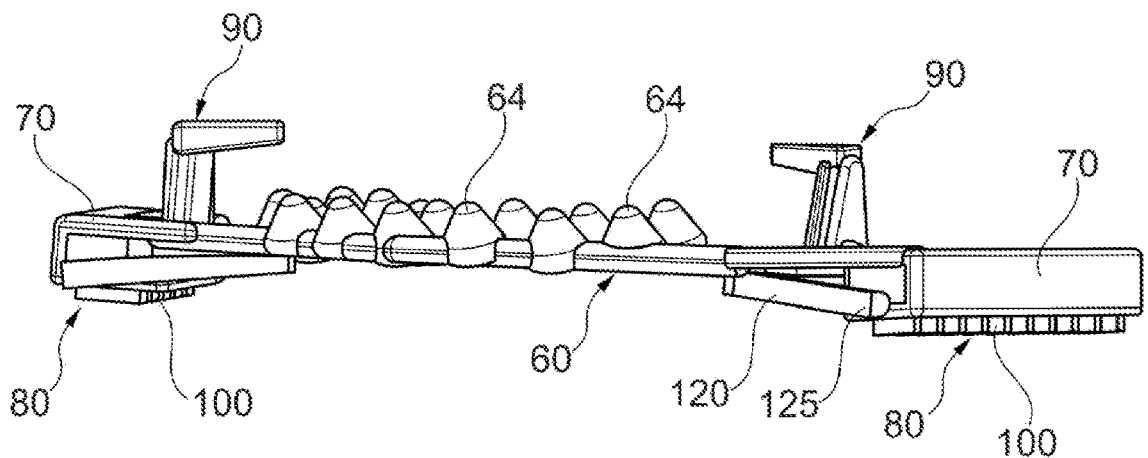
FIG. 11 shows a further exemplary embodiment which, in addition to that from FIG. 10, has housings for permanent magnets.

FIG. 11 shows a further exemplary embodiment which, in addition to that from FIG. 10, has a housing 70 for permanent magnets in order to fix the lower jaw by the magnetic force of attraction and the adhesion to the contact surfaces 80 so that it does not slide downwards in the supine position. This is also supported by the hooking of the round ridges 100 into one another, as described in connection with FIG. 6. In front of the openings of the housing 70 directed towards the incisors, closure webs 120 are fastened to the support element 60, being free in the air at their other end 125 and which can therefore be elastically bent away from the opening against their naturally existing pretension in order to be able to insert the permanent magnets or their ferritic magnets or permanent-magnetic counterparts into the housing 70. When the closure webs 120 are released, they will return to their original position as shown and block the opening so that the magnets remain securely in the housing even if the slide-on element is shaken.

Figure 12:
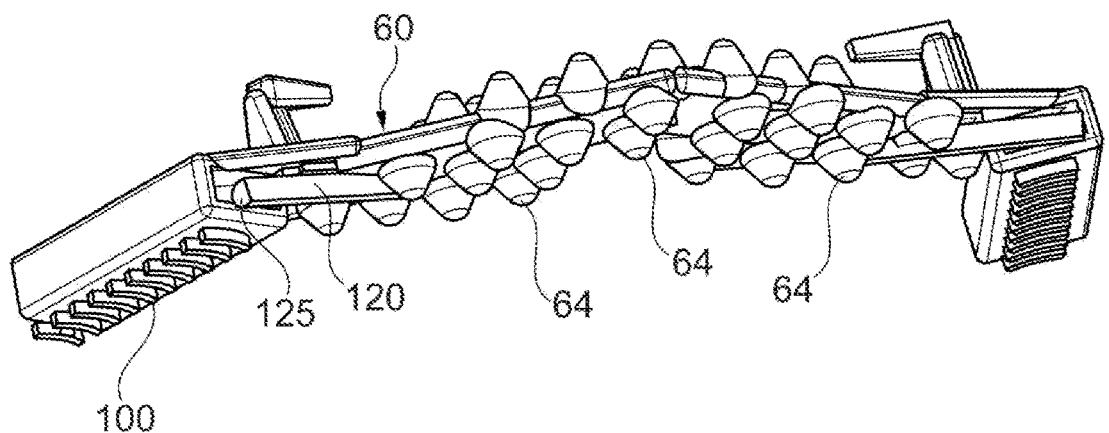
FIG. 12 shows a further exemplary embodiment which, in addition to that of FIG. 11, also bears the spiked "rough" surface on the side of the push-on element opposite the hooks, viewed from the front and slightly obliquely below, intended for use in the upper jaw.

FIG. 12 shows a further exemplary embodiment which, in addition to that from FIG. 11, also has the "rough" surface provided with the tips 64 on the side of the push-on element opposite the hooks, see also the description of FIGS. 1 to 5, from a perspective from the front and slightly oblique below when intended for use in the upper jaw.

Figure 13:
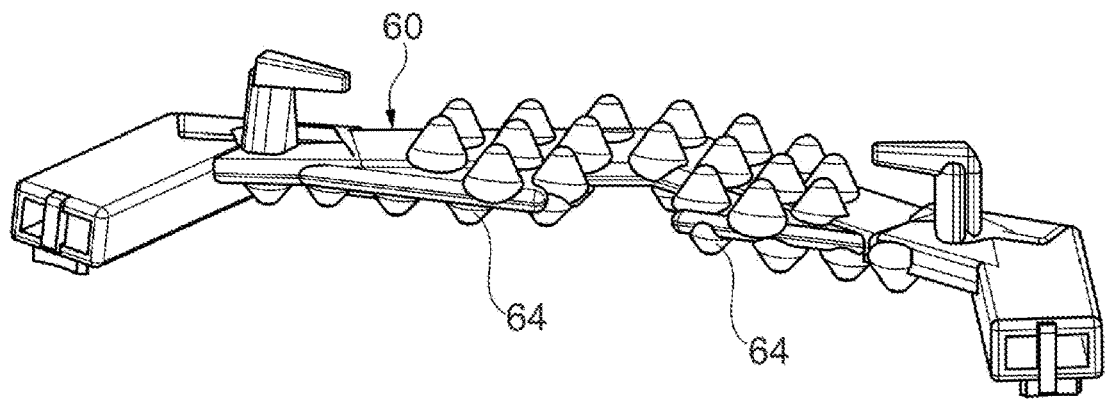
FIG. 13 shows the exemplary embodiment from FIG. 12 from a perspective from behind and slightly obliquely from above.

FIG. 13 shows the exemplary embodiment from FIG. 12 from a perspective from behind and slightly oblique from above.

According to FIGS. 12 and 13, the device according to the invention is provided with a support element 60 according to the last-mentioned embodiment, which has the non-slip surface with the gentle tips 64 on both sides, i.e. on its underside and upper side. This has the advantage that the user has the choice of placing his tongue between the anti-slip surfaces of two such devices or, as described in FIG. 11, between the palate and the anti-slip surface in order to have it held in place by the connection system according to the invention.

Although the present invention has been described above on the basis of preferred exemplary embodiments, it is not limited thereto but can be modified in many different ways.

In a particularly pronounced embodiment for users where the tooth pattern is not average because teeth are missing or the mentioned undercut locations are not available or are unusable for other reasons, the connection to the jaw is not made by a hook, but by the fact that an individual fitted bite splint adapter is integrated into the connecting body. The adapter is preferably made by a dentist from an adhesive material by means of a dental impression in such a way that it is worked closely to the teeth of the tooth area and extends just beyond the equator of the teeth in the tooth area concerned. Thus, a sufficient counterforce for holding the tongue is created by the adhesive force then existing between the adapter and the tooth area. The adapter does not necessarily have to extend over the entire dental arch, but can, for example, only include one or two or three teeth. Connector bodies can also be made that have a combination of hooks and adhesive fittings to create the counter force as needed. The fitting can then be glued to a standard connector body using a suitable adhesive, and the hook can remain or can be previously separated from the standard body.

If snap closures or connecting elements that snap into one another are used instead of the magnetically active connecting elements, the snap closures or the detents should be made in such a way that they can be opened again without any problems using the strength of the jaw muscles.

Finally, the features of the subclaims can essentially be freely combined with one another and not through the order presented in the claims, provided they are independent of one another.

The invention claimed is:

1. A device for alleviating snoring and apnea problems, with a connection system which connects the tongue to the teeth so that the tongue body is reduced or prevented from sliding into the pharyngeal area, the connection system including a bite splint which is shaped or can be shaped in such a way that it is suitable for being pushed onto one or more teeth in the lower jaw, and contains a further bite splint which is shaped or can be shaped in such a way that it is suitable for being pushed on to one or more teeth in the upper jaw,
   wherein the bite splints each have a surface facing towards the tongue, which is shaped in such a way that in contact with the surface of the tongue they cause the tongue to be slip-resistant,
   the bite splints in their molar areas or in their canine areas, respectively,
   a) are connectable to and separable from each other in mouth, and
   b) contain at least one hook each for producing a positive connection between the bite splint and an undercut location on the row of teeth, the undercut location is an interdental gap between two teeth; wherein the bite splints are connectable to and separable from each other by a permanent magnet or a magnetically attractable counterpart which is connected to the bite splint or can be connected to it by means of a positive connection and wherein a housing of said permanent magnet or said magnetically attractable counterpart comprises a pattern of ridges identical in shape, said ridges being able to hook into one another in several different positions of the housing.

2. The device according to claim 1, wherein the hooks can hook with their tip into a passage serving as an undercut location between the gums and a more or less closed joint between two teeth in the right and left molar area.

3. The device according to claim 1, wherein the hooks are formed integrally with the bite splint.

4. The device of claim 1, wherein the bite splints are connectable to and separable from each other by a snap enclosure for snapping into one another.

5. The device of claim 4, wherein a housing of said snap closure comprises a pattern of ridges identical in shape, said ridges being able to hook into one another in several different positions of the housing.

\* \* \* \* \*